US011607420B2

(12) United States Patent
Funda et al.

(10) Patent No.: US 11,607,420 B2
(45) Date of Patent: Mar. 21, 2023

(54) FORMULATION

(71) Applicant: DSM IP ASSETS B.V., Heerlen (NL)

(72) Inventors: Elger Funda, Kaiseraugst (CH); Odile Krainz, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/972,478

(22) PCT Filed: Jun. 6, 2019

(86) PCT No.: PCT/EP2019/064788
§ 371 (c)(1),
(2) Date: Dec. 4, 2020

(87) PCT Pub. No.: WO2019/234154
PCT Pub. Date: Dec. 12, 2019

(65) Prior Publication Data
US 2021/0161920 A1 Jun. 3, 2021

(30) Foreign Application Priority Data

Jun. 8, 2018 (EP) .................................... 18176695
Jul. 11, 2018 (EP) .................................... 18182946

(51) Int. Cl.
*A61K 9/20* (2006.01)
*A61K 31/655* (2006.01)
*A61K 9/50* (2006.01)
*A61K 31/525* (2006.01)
*A61K 31/606* (2006.01)

(52) U.S. Cl.
CPC .......... *A61K 31/655* (2013.01); *A61K 9/2081* (2013.01); *A61K 9/2095* (2013.01); *A61K 9/5015* (2013.01); *A61K 9/5026* (2013.01); *A61K 9/5036* (2013.01); *A61K 9/5042* (2013.01); *A61K 9/5047* (2013.01); *A61K 9/5063* (2013.01); *A61K 9/5089* (2013.01); *A61K 31/525* (2013.01); *A61K 31/606* (2013.01)

(58) Field of Classification Search
CPC .......... A61K 9/14; A61K 9/16; A61K 9/1605; A61K 9/1617; A61K 9/1623; A61K 9/20; A61K 9/2004; A61K 9/2009; A61K 9/2013; A61K 9/272
See application file for complete search history.

(56) References Cited

U.S. PATENT DOCUMENTS

2009/0004281 A1* 1/2009 Nghiem ............... A61K 31/554
424/490

OTHER PUBLICATIONS

International Search Report for PCT/EP2019/064788 dated Sep. 4, 2019, 3 pages.
Written Opinion of the ISA for PCT/EP2019/064788 dated Sep. 4, 2019, 6 pages.
Guo et al., "Diffusion of a freely water-soluble drug in aqueous enteric-coated pellets", AAPS PharmSciTech, Jun. 1, 2002, vol. 3, No. 2, 8 pages.
Rudolph et al., "A new 5-aminosalicylic acid multi-unit dosage form for the therapy of ulcerative colitis", European Journal of Pharmaceutics and Biopharmaceutics, May 1, 2001, vol. 51, No. 3, pp. 183-190 (8 total pages).
Patel et al., "Multiple Unit Pellet System (MUPS Technology) for Development of Modified Release Fast Disintegrated Tablets: A Review", Journal of Pharmaceutical & Scientific Innovation, Jul. 21, 2017, vol. 6, No. 3, pp. 50-56 (7 total pages).
Erkoboni, "Extrusion-Spheronization as a Granulation Technique", Chapter 12, 2010 (1 page).
CN Office Action (with English-language Translation), CN Appln. No. 201980037274.9, dated Mar. 22, 2022.
Hiorth et al., "Immersion coating of pellet cores consisting of chitosan and calcium intended for colon drug delivery," European Journal of Pharmaceutics and Biopharmaceutics 75 (2010) 245-253.
Li et al., "Preparation of sodium $^4$-a minosalicylic acid colon specific targeting coated tablet and its in vitro release," Chin Hosp Pharm J, Apr. 2006, vol. 26, No. 04, pp. 402-405.

* cited by examiner

*Primary Examiner* — Micah Paul Young
(74) *Attorney, Agent, or Firm* — Nixon & Vanderhye, P.C.

(57) ABSTRACT

The present invention relates to a new formulation of specific nutritional ingredients (nutraceuticals) and/or pharmaceutical compounds.

9 Claims, No Drawings

FORMULATION

CROSS-REFERENCE TO RELATED APPLICATIONS

This application is the U.S. national phase of International Application No. PCT/EP2019/064788 filed Jun. 6, 2019 which designated the U.S. and claims priority to EP 18176695.7 filed Jun. 8, 2018 and EP 18182946.6 filed Jul. 11, 2018, the entire contents of each of which are hereby incorporated by reference.

The present invention relates to a new formulation of specific nutritional ingredients (nutraceuticals) and/or pharmaceutical compounds.

The present invention is related to a formulation (mainly for oral consumption), which comprises riboflavin (as a nutritional ingredient) and (usually) a pharmaceutical compound, which is used to treat (the symptoms of) IBD (such as aminosalicylate and/or at least a pharmaceutically acceptable salt and/or at least one prodrugs thereof).

When riboflavin (also known as vitamin B2) is used in a formulation, it will show an intensive yellow color, when it is dissolved in water or even when it comes in contact with water. This leads to an unpleasant coloration of the mouth and/or the tongue of a patient who is consuming such a formulation.

The goal of the present invention was to provide a formulation (mainly for oral consumption)

The formulation for the oral consumption (usually a tablet) could be coated to solve the problem of the unwanted coloration. However, in case the specific nutritional ingredients (nutraceuticals) and/or pharmaceutical compounds are to be delivered to the small or large intestine a regular coating of the tablet might not be the ideal solution, e.g. due to large variations of residence time in the stomach or dose dumping effect.

There is a need of formulations, which do not have the disadvantages are described above.

Therefore, it was found that the coloration issue of the riboflavin (in combination with the IBD drugs) can be solved by using a multiple-unit pellet system (MUPS), wherein the riboflavin particles are coated.

Riboflavin, also known as vitamin B2, is a micronutrient with a key role in maintaining health in humans and other mammals. It is the central component of the cofactors FAD and FMN, and is therefore required by all flavoproteins. As such, riboflavin is required for a wide variety of cellular processes. It plays a key role in energy metabolism, and for the metabolism of fats, ketone bodies, carbohydrates, and proteins. Riboflavin is found naturally in asparagus, popcorn, bananas, per-simmons, okra, chard, cottage cheese, milk, yogurt, meat, eggs, fish, and green beans. Other sources specify cheese, leafy green vegetables, liver, kidneys, legumes, tomatoes, yeast, mushrooms, and almonds. Recently it has been shown that Riboflavin has a beneficial effect on growth of *Faecalibacterium prausnitzii,* which is a marker species for a healthy gut.

An aminosalicylate is a class of medications that is often used to treat IBD and/or IBS. In the context of the present invention the class of aminosalicylates consists of 4-aminosalicylic acid, Balsalazide, Olsalazine, Sulfasalazine and Mesalazine (5-Aminosalicylic acid). Furthermore, instead of the Aminosalicylate any other IBD drug can be used, such as immune system suppressors (such as Azathioprine, Mercaptopurine, Methotrexate, Levamisole, Cyclosporine, Infliximab, Adalimumab and golimumab) or antibiotics (such as ciprofloxacin and metronidazole). If needed also mixture of such IBD drugs can be used.

Multiple unit pellet systems (MUPS) are well known in the field of pharmaceutical applications. They are described in many patent applications as well as scientific papers. Also the production of MUPS is described and well known. MUPS as therapeutical dosage forms can either be used as such, e.g. as granulate in a sachet or they can be integrated in other dosage forms like tablets or capsules.

The present invention relates to a multiple unit pellet system, which comprises at least two different particles
  (a) pellets (pellets (a)) comprising riboflavin and
  (b) particles (particles (b)) comprising at least one aminosalicylate and/or at least a pharmaceutically acceptable salt and/or at least one prodrugs thereof,
  wherein the pellets (a) are coated.

Pellets (a), which comprise riboflavin can comprise between 10-90 wt-% based on the total weight of the pellet (a). Preferably 15-75 wt-%.

Particles (b), can be any kind of particles (such as powders, granules, beadlets and pellets, as well as any mixture of them) which comprise the IBD drug(s) can comprise between 0.5-95 wt-% based on the total weight of the particle (a). Preferably 1-50 wt-%. (the content depends on the kind of the particle (powder do have a much higher content than a beadlet for example).

Furthermore, instead of the Aminosalicylate any other IBD drug can be used in particle (b), such as immune system suppressors (such as Azathioprine, Mercaptopurine, Methotrexate, Levamisole, Cyclosporine, Infliximab, Adalimumab and golimumab) or antibiotics (such as ciprofloxacin and metronidazole). If needed also mixture of such IBD drugs can be used.

Suitable coating materials for the pellets are such, which release the riboflavin (and if coated also the least one aminosalicylate and/or at least a pharmaceutically acceptable salt and/or at least one prodrugs thereof) in the small or large intestine.

Suitable coating material are polymers, which are derivatives of acrylic acid and cellulose. Various pH-dependent coating polymers include cellulose acetate phthalate (CAP) (Aquateric®), poly vinyl acetate phthalate (PVAP) (Coateric®), hydroxypropyl methyl cellulose phthalate (HPMCP), and methacrylic acid copolymers, commonly known as methacrylate copolymers or Eudragit.

Shellac and fats are also suitable coating materials.

Also suitable materials for the coating are for example alginate, chitosan, pectin, cyclodextrin as well as other gums. Preferred are alginate or pectin. This kind of coating might be crosslinked. The crosslinking can be done by commonly known crosslinking compounds. In case alginate is used that can be done by Mg and/or Ca ion (by the use of a salt). The crosslinker can be sprayed onto to pellet after having applied coating material or simultaneously. Or the coated pellets can be dipped into a solution comprising the crosslinker. Preferably the crosslinker is sprayed onto the particles after having applies the coating layer.

The coating layer is usually covering the pellet (more or less) completely.

Typically, the layer thickness of the coating layer is at least 10 µm. Preferably, thickness of the coating layer is at least 50-70 µm. Required layer thickness is determined by barrier properties of the coating material. To achieve such coating layer thickness, the amount of coating material is at least 10% (w/w) of the coated particle. Typically, the amount of coating material is at least 20% (w/w) of the coated particle.

The coating of pellet (a) is about 5-60 wt-%, based on the total weight of the pellet (a). In case particle (b) is coated then the coating is about 5-60 wt-%, based on the total weight of the particle (b).

It is clear, that MUPS tablets according to the present invention comprises the usual auxiliary ingredients, which are needed to form tablet.

Such auxiliary ingredients are for example, binders, fillers, lubricants, proteins, dyes, flavors, sweeteners, minerals, and antioxidants without being limited thereto.

Particularly suitable fillers according to the present invention encompass mono-, di- and tri-calcium phosphate, limestone (calcium carbonate), magnesium carbonate, silicate compounds (magnesium and aluminum silicate), magnesiumoxide, microcrystalline cellulose, proteins, silicon dioxide as well as mixtures thereof, such as more in particular microcrystalline wax, microcrystalline cellulose and limestone as well as mixtures thereof, most preferably microcrystalline cellulose.

Particularly suitable lubricants according to the present invention are water insoluble lubricants and encompass magnesium stearate, calcium stearate, zinc stearate or stearic acid such as more in particular magnesium stearate and/or calcium stearate.

If present, the total amount of the auxiliary ingredients can be up to 99 wt-%, based on the total weight of the MUPS tablet. Usually between 10-80 wt-%.

The MUPS tablets according to the present invention are compressed tablets, which depending on the process of production as well as the storage conditions, may comprise some water. Generally, the moisture content of the tablets according to the present invention is below 5 wt-%, based on the total weight of the MUPS tablet.

The MUPS tablet usually comprises up to 40 wt.-%, based on the total weight of the MUPS tablet, of pellets, The MUPS tablets according to the invention are preferably un-coated. If needed or desired the MUPS tablets could also be coated.

More preferably, the MUPS tablets according to the invention have a tablet weight of 100 to 1000 mg, preferably 300 to 900 mg.

The MUPS tablets according to the invention are produced by the following process
(i) the pellets (a) and the powder or particles (b) are produced—
(ii) the pellets (a) and optionally the particles (b) are coated
(iii) the pellets and the particles are mixed
(iv) optionally other ingredients, which are useful or desired to form the tablet are added
(v) compressing the mixture obtained in step (iii) or step (iv) into a tablet.

The pharmaceutical compositions according to the invention are intended for oral use and can be used in the dosage form of an uncoated MUPS tablet or a film-coated MUPS tablet.

A further object of the invention are MUPS tablets obtainable by a process according to the invention.

The MUPS tablets can be of any size and shape, preferably the MUPS tablets can be of sizes from 21.0×10.0×9.0 to 11.0×5.0×3.0 mm, preferably from 21.0×10.0×9.0 to 14.0×6.0×4.0 mm, most preferred from 21.0×10.0×8.0 mm to 15.0×7.0×4.0 mm.

It also possible that the pellet (b) are coated. Usually the same kind of coating material as described and disclosed for the pellets (a) are used. It is not essential that the pellets (a) and the pellets (b) are the identical coating material when used in a MUPS tablet.

The same applies for pellets (a). It possible to use more than one coating material. This means that a certain amount of the pellets are coated with one coating material, whereas another amount of the pellets are coated with another coating material.

The following examples serve to illustrate specific embodiments of the invention claimed herein. All percentages are given in relation to the weight and all the temperatures are given in degree Celsius.

EXAMPLES

Example 1: Coating with Alginate/Shellac 80 g granulated Riboflavin was successively coated with 9% Na-alginate, 1% Ca-Chloride and 25% shellac using a WFP-mini fluid bed processor (DMR) in Wurster configuration. 89 g coated product with particle size between 250 and 1000 µm was obtained. Coating material was 35% of the particle mass, riboflavin content 50%.

20 mg of coated powder (containing 10 mg of Riboflavin) was dissolved in 1000 ml water for 15 min. Absorption of the solution was measured at 545 nm using a spectrophotometer (Genesys 20, thermo Scientific). Absorption of the solution was 0.065.

Comparison Example 2: Solution of Uncoated Riboflavin 10 mg of riboflavin powder was dissolved in 1000 ml water for 15 min. Absorption of the solution was measured at 545 nm using a spectrophotometer (Genesys 20, thermo Scientific). Absorption of the solution was 0.386.

Example 3: Coating with Eudragit FS30D 80 g granulated Riboflavin was coated with 60 g Eudragit FS30D and 10 g PlasACRYL T20 using a WFP-mini fluid bed processor (DMR) in Wurster configuration. 71 g coated product with particle size between 250 and 1000 µm was obtained. Coating material was ca. 20% of the particle mass, riboflavin content was 60%.

16.6 mg of coated powder (containing 10 mg of Riboflavin) was dissolved in 1000 ml water for 15 min. Absorption of the solution was measured at 545 nm using a spectrophotometer (Genesys 20, thermo Scientific). Absorption of the solution was 0.087.

The invention claimed is:

1. A multiple unit pellet system in the form of a tablet having a weight of 100 to 1000 mg which comprises a compressed mixture of pellets (a) and particles (b), wherein
each of the pellets (a) has a coating layer of a coating material and comprises 15-75 wt. %, based on total weight of the pellets (a), of riboflavin, and wherein
each of the particles (b) comprise at least one aminosalicylate and/or at least a pharmaceutically acceptable salt and/or at least one prodrug thereof.

2. The multiple unit pellet system according to claim 1, which further comprises at least one auxiliary ingredient.

3. The multiple unit pellet system according to claim 2, wherein the at least one auxiliary ingredient is selected from the group consisting of binders, fillers, lubricants, proteins, dyes, flavours, sweeteners, minerals, and antioxidants.

4. The multiple unit pellet system according to claim 2, wherein the total amount of the auxiliary ingredients is up to 99 wt. %, based on the total weight of the tablet.

5. The multiple unit pellet system according to claim 1, wherein the particles (b) comprise at least one aminosalicylate and/or at least a pharmaceutically acceptable salt and/or at least one prodrug thereof which is selected from the group consisting of 4-aminosalicylic acid, Balsalazide, Olsalazine, Sulfasalazine and Mesalazine (5-Aminosalicylic acid).

6. The multiple unit pellet according to claim 1, wherein the coating material is selected from the group consisting of ogcellulose acetate phthalate (CAP), polyvinyl acetate phthalate (PVAP), hydroxypropyl methyl cellulose phthalate (HPMCP), methacrylic acid copolymers, shellac, fats, alginate, chitosan, pectin, cyclodextrin and gums.

7. The multiple unit pellet according to claim 6, wherein the coating layer of the coating material on the pellets (a) has a thickness of 50-70 μm.

8. The multiple unit pellet according to claim 7, wherein the coating material is present in an amount which is 5-60 wt. %, based on the total weight of the pellets (a).

9. A process for the production of the multiple unit pellet system according to claim 1, comprising the steps of:
   (i) providing the pellets (a) and the particles (b);
   (ii) coating at least the pellets (a) with a coating material;
   (iii) forming a compressible mixture by mixing the pellets (a) and the particles (b);
   (iv) optionally adding other ingredients to the compressible mixture formed according to step (iii); and
   (v) compressing the compressible mixture into the tablet form of the multiple unit pellet system.

\* \* \* \* \*